US012118650B2

(12) United States Patent
O'Connor et al.

(10) Patent No.: US 12,118,650 B2
(45) Date of Patent: Oct. 15, 2024

(54) SYSTEMS AND METHODS FOR RENDERING OBJECTS TRANSLUCENT IN X-RAY IMAGES

(71) Applicant: Nuvasive, Inc., San Diego, CA (US)

(72) Inventors: Sean O'Connor, San Diego, CA (US); Alexander Hsu, San Diego, CA (US); Kara Robinson, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 414 days.

(21) Appl. No.: 17/760,602

(22) PCT Filed: Sep. 16, 2020

(86) PCT No.: PCT/US2020/051138
§ 371 (c)(1),
(2) Date: Mar. 15, 2022

(87) PCT Pub. No.: WO2021/055522
PCT Pub. Date: Mar. 25, 2021

(65) Prior Publication Data
US 2022/0343567 A1     Oct. 27, 2022

Related U.S. Application Data

(60) Provisional application No. 62/900,806, filed on Sep. 16, 2019.

(51) Int. Cl.
| | |
|---|---|
| *G06T 11/00* | (2006.01) |
| *A61B 90/00* | (2016.01) |
| *G06T 7/00* | (2017.01) |
| *G06T 7/32* | (2017.01) |
| *G06V 20/60* | (2022.01) |
| *G16H 30/40* | (2018.01) |

(52) U.S. Cl.
CPC ............ *G06T 11/008* (2013.01); *A61B 90/37* (2016.02); *G06T 7/0012* (2013.01); *G06T 7/32* (2017.01); *G06V 20/60* (2022.01); *G16H 30/40* (2018.01); *G06T 2200/04* (2013.01); *G06T 2207/10116* (2013.01); *G06T 2207/20212* (2013.01); *G06T 2207/30004* (2013.01); *G06T 2211/40* (2013.01); *G06V 2201/034* (2022.01)

(58) Field of Classification Search
None
See application file for complete search history.

(56) References Cited

U.S. PATENT DOCUMENTS

| | | | |
|---|---|---|---|
| 2003/0095626 A1* | 5/2003 | Anderton | G06T 5/94 378/98.7 |
| 2013/0195338 A1* | 8/2013 | Xu | G06T 7/33 382/131 |
| 2013/0267838 A1 | 10/2013 | Fronk et al. | |
| 2016/0117823 A1* | 4/2016 | Isaacs | G06T 11/60 715/863 |

(Continued)

OTHER PUBLICATIONS

PCT International Search Report for PCT Application No. PCT/US2020/051138 mailed Jan. 15, 2021 (6 pages).

(Continued)

*Primary Examiner* — Dung D Tran

(57) ABSTRACT

The present disclosure includes systems, methods and media for rendering objects translucent and for recovery of anatomical information blocked by the objects in medical images.

20 Claims, 7 Drawing Sheets

(56) References Cited

U.S. PATENT DOCUMENTS

2017/0165008 A1* 6/2017 Finley .................. A61B 6/4441
2021/0330393 A1* 10/2021 Govari .................. G06T 7/0012
2022/0392085 A1* 12/2022 Finley ....................... G06T 7/70

OTHER PUBLICATIONS

PCT Written Opinion for PCT Application No. PCT/US2020/051138 mailed Jan. 15, 2021 (6 pages).
Chen et al., "Development of a Surgical Navigation System Based on Augmented Reality Using an Optical See-Through Head-Mounted Display," Journal of Biomedical Informatics, 2015, 55:124-131.
Livingston et al., "Pursuit of 'X-Ray Vision' for Augmented Reality," Human Factors in Augmented Reality Environments, 2013, pp. 67-107.

* cited by examiner

Fig. 1b    106
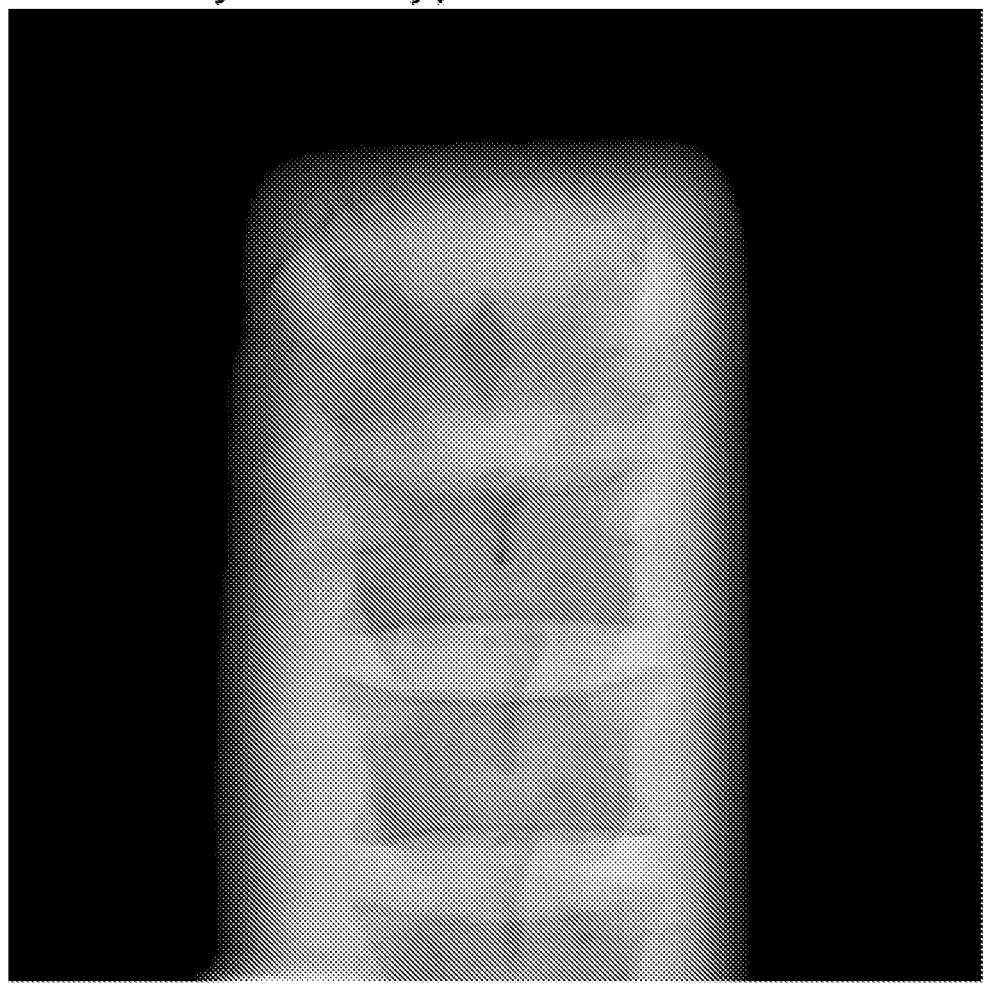

108

Composite mask used

SYSTEMS AND METHODS FOR RENDERING OBJECTS TRANSLUCENT IN X-RAY IMAGES

CROSS REFERENCE

This application is a National Stage Application of PCT/US2020/051138, filed Sep. 16, 2020, which is a non-provisional of, and claims the benefit of, U.S. Provisional patent application Ser. No. 62/900,806 filed Sep. 16, 2019, the entire contents of which are hereby expressly incorporated by reference into this disclosure as if set forth in their entirety herein.

BACKGROUND

Medical images, such as radiographic images, collected during surgery can contain opaque surgical instruments in the field of view, for example, metal retractors, metal clamps, or forceps. Surgeons may find it useful to visualize both the exact placement of the instruments, and what anatomy is obstructed from view by the instruments.

Certain surgical instruments may be required in order to properly perform a surgery. However, surgical instruments in the field of view of radiographic image can often block the view of anatomy of interest, particularly dense metal materials, thereby hindering the surgery. Thus, there is a need to remove the metal instruments or other radiodense items in radiographic images and restore the anatomy blocked by these instruments to ensure accurate and complete presentation of anatomical information needed in order to successfully perform the medical procedure. Alternatively, surgeons may want to be able to alter the translucency of the objects arbitrarily depending on the step of the medical procedure.

With a single image, such opaque objects cannot be removed from view in the image because no knowledge of the anatomy blocked by them can be obtained. Currently, to visualize both the instruments and the blocked anatomy, two images with aligned anatomy can be displayed to the surgeon, one image can be with opaque instrument and the other without. However, this method does not apply when only one image is present, or if both images contain opaque items blocking the anatomy of interest. Further, acquiring two images with aligned anatomy may introduce additional ionizing radiation to the patient, posing a potential health risk to the patient and surgical staff. Thus, there is an urgent and unmet need to provide surgeons information of the opaque instruments as well as the anatomy blocked by the instruments without adding exposure of the patient to ionizing radiation.

SUMMARY

Disclosed herein are systems, methods, and media for rendering opaque instruments, e.g., metal at a translucency level preferred by the surgeon. The systems, methods, and media herein advantageously utilize a three-dimensional (3D) scan dataset such as a computed tomography ("CT") scan to provide images of obstructed anatomy. Pre-operative 3D scans may be readily available before the surgery, so that there is no need to acquire additional radiographic images or adding radiation exposure to the patient during a surgery. The 3D scan dataset herein can be registered to a two-dimensional (2D) radiographic image so that the perspective (e.g., position and orientation) relative to the 3D dataset in the two-dimensional (2D) image can be predicted. In some embodiments, registering a 3D dataset includes registering the coordinate system of the 3D scan to the 2D image space. In some embodiments, the 3D dataset can be registered with a 2D image using the same tracked instrument(s). Once the 3D dataset is registered to the 2D image space, a prediction 2D image can be generated using the 3D dataset by predicting what 2D image can be generated from the 3D dataset from the perspective of the camera. Assuming correct registration, the prediction of the 3D dataset will perfectly match (overlap with) the anatomy in the actual 2D image.

The methods, systems, and media disclosed herein advantageously provide the capability to make metal appear translucent and recover visualization of the anatomy blocked by the opaque objects accurately even if only one 2D image is taken, or if all 2D images contain opaque items. The methods, systems, and media disclosed herein can be employed if no 2D images have been taken yet, as a non-limiting example, a prediction of the entire image can be displayed, with an overlay of any opaque instruments whose location are being tracked.

In one aspect, disclosed herein is a method for rendering opaque objects translucent in medical images, the method comprising: receiving, by a computer, a three-dimensional dataset of a subject; determining, by the computer, an imaging space of an image capturing device, wherein the image capturing device is configured to generate a two-dimensional image of the subject from the imaging space; acquiring, by the image capturing device, a two-dimensional image of the subject from the imaging space; registering, by the computer, the three-dimensional dataset of the subject to the imaging space of the image capturing device, thereby generating a registered three-dimensional dataset; and predicting, by the computer, at least part of the two-dimensional image of the subject using the registered three-dimensional dataset, wherein the at least part of the two-dimensional image of the subject includes one or more metal or otherwise opaque objects, and wherein the prediction of the at least part of the two-dimensional image of the subject includes a first set of anatomical information of the subject that is blocked by the one or more metal objects. In some cases, the method further comprises receiving, by the computer, the two-dimensional image of the subject from the image capturing device. In some cases, the method further comprises, subsequent to the step of predicting at least a part of the two-dimensional image of the subject, generating, by the computer, an improved two-dimensional image of the subject based on the two-dimensional image and the prediction of the at least part of the two-dimensional image of the subject. In some cases, the improved two-dimensional image is unobscured by the one or more metal objects, and wherein the improved two-dimensional image includes the first set of anatomical information of the subject. In some cases, generating the improved two-dimensional image of the subject comprises: identifying, by the computer, a plurality of pixels that at least partly contains the one or more metal or otherwise opaque objects; optionally modifying, by the computer, data of the plurality of pixels; and combining, by the computer, the prediction of the at least part of the two-dimensional image of the subject and the data of the plurality of pixels pixel by pixel. In some cases, the two-dimensional image is an X-ray image, and wherein the one or more metal or otherwise opaque objects block the first set of anatomical information of the subject therewithin. In some cases, the method further comprises adjusting registration of the three-dimensional dataset of the subject to the imaging space of the image capturing device until prediction of a second set of unblocked anatomical information of the two-dimensional image satisfies a pre-determined criterion.

In some cases, adjusting registration of the three-dimensional dataset of the subject to the imaging space of the image capturing device comprises calculating a similarity of the prediction of the second set of unblocked anatomical information to the second set of unblocked anatomical information in the two-dimensional image. In some cases, the two-dimensional image is generated using projection imaging, and wherein the one or more metal objects block the first set of anatomical information of the subject within the two-dimensional image. In some cases, the three-dimensional dataset includes a CT dataset, a Magnetic Resonance Imaging dataset, a Positron Emission Tomography (PET) dataset, or an Ultrasound dataset of the subject. In some cases, the three-dimensional dataset is acquired prior to a medical procedure of the subject that includes introduction of metal objects to the subject, or wherein the three-dimensional dataset is free of the one or more metal objects. In some cases, the method further comprises, presenting, by a digital display, the improved two-dimensional image to a user during a medical procedure. In some cases, presenting the improved two-dimensional image comprises presenting the prediction of the first set of blocked anatomical information as an overlay superimposed on the two-dimensional image thereby facilitating the medical procedure. In some cases, one or more of: the registering of the three-dimensional dataset of the subject to the imaging space of the image capturing device; the prediction of the at least part of the two-dimensional image of the subject using the registered three-dimensional dataset; and the presentation of the improved two-dimensional image to the user is in real-time. In some cases, the real-time includes a time duration of less than 1 second, 0.8 seconds, 0.6 seconds, 0.5 seconds, 0.4 seconds, 0.3 seconds, 0.2 seconds, 0.1 seconds, 0.08 seconds, 0.06 seconds, 0.05 seconds, 0.02 seconds, or 0.01 seconds. In some cases, registering the three-dimensional dataset of the subject to the imaging space of the image capturing device comprises registering a first coordinate system of the three-dimensional dataset to a second coordinate system of the imaging space. In some cases, the three-dimensional dataset is acquired with metal items within a field of view thereof, and wherein registering the three-dimensional dataset of the subject to the imaging space of the image capturing device comprises tracking the metal items using infrared light in the imaging space and registering the metal item in the three-dimensional dataset to the metal item in the imaging space.

In another aspect, disclosed herein is a computer-implemented system comprising: an image capturing device; a digital processing device comprising a processor, a memory, and an operating system configured to perform executable instructions, the digital processing device in digital communication with the image capturing device; and a computer program stored in the memory including instructions executable by the processor of the digital processing device to create a metal object removal application comprising: a software module configured to receive a three-dimensional dataset of a subject; a software module configured to determine by the computer, an imaging space of an image capturing device, wherein the image capturing device is configured to generate a two-dimensional image obtained of the subject from the imaging space; a software module configured to register the three-dimensional dataset of the subject to the imaging space of the image capturing device, thereby generating a registered three-dimensional dataset; and a software module configured to predict at least part of the two-dimensional image of the subject using the registered three-dimensional dataset, wherein the at least part of the two-dimensional image of the subject includes one or more metal objects, and wherein the prediction of the at least part of the two-dimensional image of the subject includes a first set of anatomical information of the subject that is blocked by the one or more metal objects.

In another aspect, disclosed herein is non-transitory computer-readable storage media encoded with a computer program including instructions executable by a processor to create a metal object removal application, the media comprising: a software module configured to receive a three-dimensional dataset of a subject; a software module configured to determine by the computer, an imaging space of an image capturing device, wherein the image capturing device is configured to generate a two-dimensional image obtained of the subject from the imaging space; a software module configured to register the three-dimensional dataset of the subject to the imaging space of the image capturing device, thereby generating a registered three-dimensional dataset; and a software module configured to predict at least part of the two-dimensional image of the subject using the registered three-dimensional dataset, wherein the at least part of the two-dimensional image of the subject includes one or more metal objects, and wherein the prediction of the at least part of the two-dimensional image of the subject includes a first set of anatomical information of the subject that is blocked by the one or more metal objects.

In yet another aspect, disclosed herein is a method for rendering objects translucent in medical images, the method comprising: receiving, by a computer, a three-dimensional dataset of a subject; determining, by the computer, an imaging space of an image capturing device, wherein the image capturing device is configured to generate a two-dimensional image of the subject from the imaging space; registering, by the computer, the three-dimensional dataset of the subject to the imaging space of the image capturing device, thereby generating a registered three-dimensional dataset; predicting, by the computer, at least part of the two-dimensional image of the subject using the registered three-dimensional dataset, wherein the at least part of the two-dimensional image of the subject includes the one or more objects, and wherein the prediction of the at least part of the two-dimensional image of the subject includes a first set of anatomical information of the subject that is blocked by the one or more objects. In some cases, the method herein is without introduction of a radiation dosage to the subject. In some cases, the method further comprises acquiring, by the image capturing device, a two-dimensional image of the subject from the imaging space; and receiving, by the computer, the two-dimensional image of the subject from the image capturing device. In some cases, the method further comprises subsequent to the step of predicting at least a part of the two-dimensional image of the subject, generating, by the computer, an improved two-dimensional image of the subject based on the two-dimensional image and the prediction of the at least part of the two-dimensional image of the subject. In some cases, the improved two-dimensional image is unobscured by the one or more metal objects, and wherein the improved two-dimensional image includes the first set of anatomical information of the subject. In some cases, generating, by the computer, the improved two-dimensional image of the subject is without introduction of a radiation dosage to the subject. In some cases, the one or more objects comprise metal.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1b shows an exemplary 3D CT image dataset of the same subject without the metal objects, in accordance with embodiments herein;

DETAILED DESCRIPTION

Figure 1A:
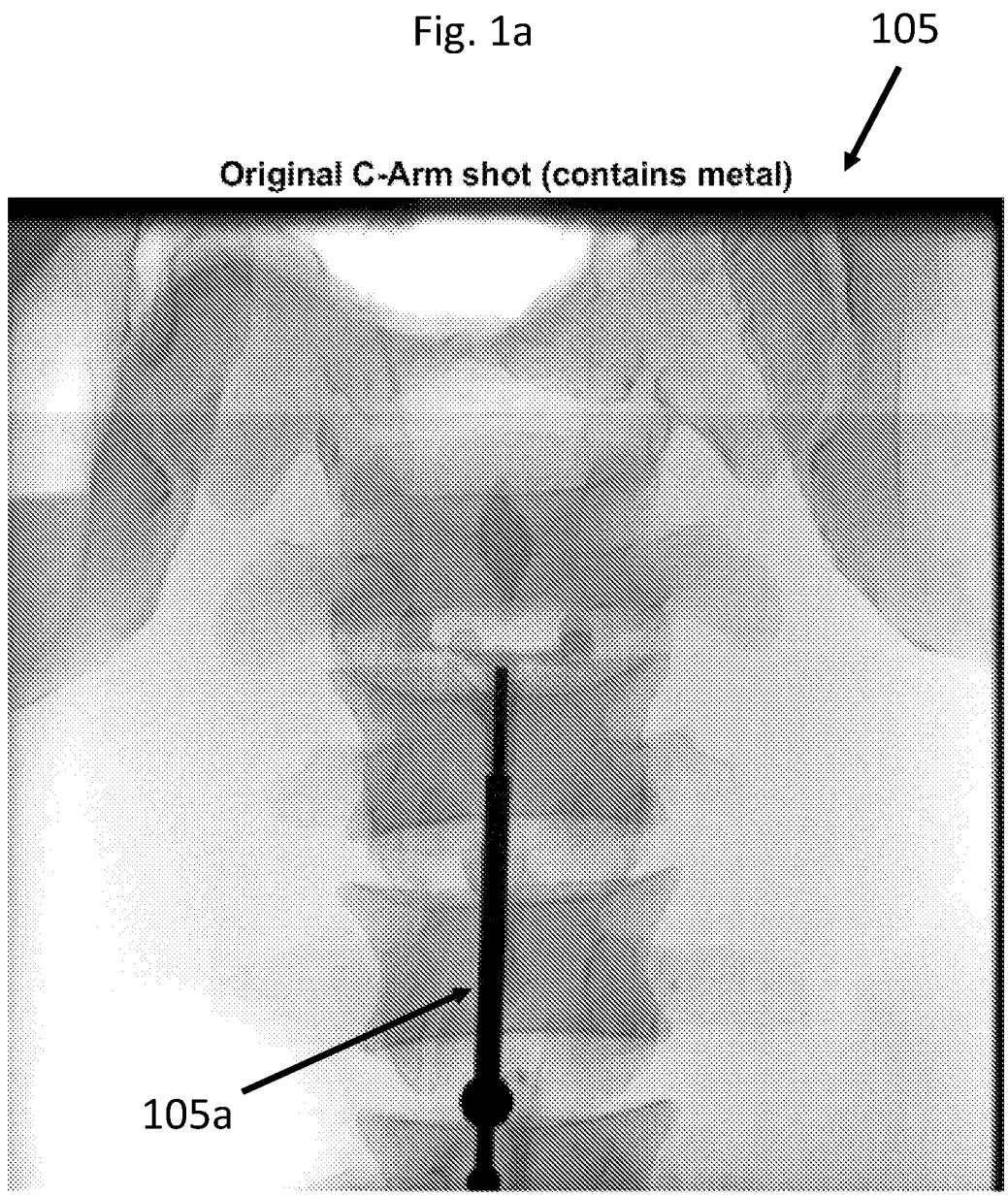
FIG. 1a shows an exemplary 2D radiographic image that contains metal object(s), in accordance with embodiments herein.
Figure 1C:
FIG. 1c shows an improved 2D X-ray image of FIG. 1a, in which the metal object(s) has been removed, in accordance with embodiments herein.

Disclosed herein, in some embodiments, is a method for rendering metal objects translucent in medical images, the method comprising: receiving, by a computer, a three-dimensional dataset of a subject; determining, by the computer, an imaging space of an image capturing device, wherein the image capturing device is configured to generate a two-dimensional image of the subject from the imaging space; acquiring, by the image capturing device, a two-dimensional image of the subject from the imaging space; registering, by the computer, the three-dimensional dataset of the subject to the imaging space of the image capturing device, thereby generating a registered three-dimensional dataset; and predicting, by the computer, at least part of the two-dimensional image of the subject using the registered three-dimensional dataset, wherein the at least part of the two-dimensional image of the subject includes one or more metal objects, and wherein the prediction of the at least part of the two-dimensional image of the subject includes a first set of anatomical information of the subject that is blocked by the one or more metal objects. In some cases, the method further comprises receiving, by the computer, the two-dimensional image of the subject from the image capturing device. In some cases, the method further comprises, subsequent to the step of predicting at least a part of the two-dimensional image of the subject, generating, by the computer, an improved two-dimensional image of the subject based on the two-dimensional image and the prediction of the at least part of the two-dimensional image of the subject. In some cases, the improved two-dimensional image is unobscured by the one or more metal objects, and wherein the improved two-dimensional image includes the first set of anatomical information of the subject. In some cases, generating the improved two-dimensional image of the subject comprises: identifying, by the computer, a plurality of pixels that at least partly contains the one or more metal objects; optionally modifying, by the computer, data of the plurality of pixels; and combining, by the computer, the prediction of the at least part of the two-dimensional image of the subject and the data of the plurality of pixels pixel by pixel. In some cases, the two-dimensional image is an X-ray image, and wherein the one or more metal objects block the first set of anatomical information of the subject therewithin. In some cases, the method further comprises adjusting registration of the three-dimensional dataset of the subject to the imaging space of the image capturing device until prediction of a second set of unblocked anatomical information of the two-dimensional image satisfies a pre-determined criterion. In some cases, adjusting registration of the three-dimensional dataset of the subject to the imaging space of the image capturing device comprises calculating a similarity of the prediction of the second set of unblocked anatomical information to the second set of unblocked anatomical information in the two-dimensional image. In some cases, the two-dimensional image is generated using projection imaging, and wherein the one or more metal objects block the first set of anatomical information of the subject within the two-dimensional image. In some cases, the three-dimensional dataset includes a CT dataset, a Magnetic Resonance Imaging dataset, a Positron Emission Tomography (PET) dataset, or an Ultrasound dataset of the subject. In some cases, the three-dimensional dataset is acquired prior to a medical procedure of the subject that includes introduction of metal objects to the subject, or wherein the three-dimensional dataset is free of the one or more metal objects. In some cases, the method further comprises, presenting, by a digital display, the improved two-dimensional image to a user during a medical procedure. In some cases, presenting the improved two-dimensional image comprises presenting the prediction of the first set of blocked anatomical information as an overlay superimposed on the two-dimensional image thereby facilitating the medical procedure. In some cases, one or more of: the registering of the three-dimensional dataset of the subject to the imaging space of the image capturing device; the prediction of the at least part of the two-dimensional image of the subject using the registered three-dimensional dataset; and the presentation of the improved two-dimensional image to the user is in real-time. In some cases, the real-time includes a time duration of less than 1 second, 0.8 seconds, 0.6 seconds, 0.5 seconds, 0.4 seconds, 0.3 seconds, 0.2 seconds, 0.1 seconds, 0.08 seconds, 0.06 seconds, 0.05 seconds, 0.02 seconds, or 0.01 seconds. In some cases, registering the three-dimensional dataset of the subject to the imaging space of the image capturing device comprises registering a first coordinate system of the three-dimensional dataset to a second coordinate system of the imaging space. In some cases, the three-dimensional dataset is acquired with metal items within a field of view thereof, and wherein registering the three-dimensional dataset of the subject to the imaging space of the image capturing device comprises tracking the metal items using infrared light in the imaging space and registering the metal pins in the three-dimensional dataset to the metal pins in the imaging space.

Disclosed herein, in some embodiments, is a computer-implemented system comprising: an image capturing device; a digital processing device comprising a processor, a memory, and an operating system configured to perform executable instructions, the digital processing device in digital communication with the image capturing device; and a computer program stored in the memory including instructions executable by the processor of the digital processing device to create a metal object removal application comprising: a software module configured to receive a three-dimensional dataset of a subject; a software module configured to determine by the computer, an imaging space of an image capturing device, wherein the image capturing device is configured to generate a two-dimensional image obtained of the subject from the imaging space; a software module configured to register the three-dimensional dataset of the subject to the imaging space of the image capturing device, thereby generating a registered three-dimensional dataset; and a software module configured to predict at least part of the two-dimensional image of the subject using the registered three-dimensional dataset, wherein the at least part of the two-dimensional image of the subject includes one or more metal objects, and wherein the prediction of the at least part of the two-dimensional image of the subject includes a first set of anatomical information of the subject that is blocked by the one or more metal objects.

Disclosed herein, in some embodiments, is non-transitory computer-readable storage media encoded with a computer program including instructions executable by a processor to create a metal object removal application, the media comprising: a software module configured to receive a three-dimensional dataset of a subject; a software module configured to determine by the computer, an imaging space of an image capturing device, wherein the image capturing device is configured to generate a two-dimensional image obtained of the subject from the imaging space; a software module configured to register the three-dimensional dataset of the subject to the imaging space of the image capturing device, thereby generating a registered three-dimensional dataset; and a software module configured to predict at least part of the two-dimensional image of the subject using the registered three-dimensional dataset, wherein the at least part of the two-dimensional image of the subject includes one or more metal objects, and wherein the prediction of the at least part of the two-dimensional image of the subject includes a first set of anatomical information of the subject that is blocked by the one or more metal objects.

Disclosed herein, in some embodiments, is a method for rendering objects translucent in medical images, the method comprising: receiving, by a computer, a three-dimensional dataset of a subject; determining, by the computer, an imaging space of an image capturing device, wherein the image capturing device is configured to generate a two-dimensional image of the subject from the imaging space; registering, by the computer, the three-dimensional dataset of the subject to the imaging space of the image capturing device, thereby generating a registered three-dimensional dataset; predicting, by the computer, at least part of the two-dimensional image of the subject using the registered three-dimensional dataset, wherein the at least part of the two-dimensional image of the subject includes the one or more objects, and wherein the prediction of the at least part of the two-dimensional image of the subject includes a first set of anatomical information of the subject that is blocked by the one or more objects. In some cases, the method herein is without introduction of a radiation dosage to the subject. In some cases, the method further comprises acquiring, by the image capturing device, a two-dimensional image of the subject from the imaging space; and receiving, by the computer, the two-dimensional image of the subject from the image capturing device. In some cases, the method further comprises subsequent to the step of predicting at least a part of the two-dimensional image of the subject, generating, by the computer, an improved two-dimensional image of the subject based on the two-dimensional image and the prediction of the at least part of the two-dimensional image of the subject. In some cases, the improved two-dimensional image is unobscured by the one or more metal objects, and wherein the improved two-dimensional image includes the first set of anatomical information of the subject. In some cases, generating, by the computer, the improved two-dimensional image of the subject is without introduction of a radiation dosage to the subject. In some cases, the one or more objects comprise metal.

Certain Terms

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As disclosed herein, the objects, instruments, and/or surgical tools to be rendered using the methods, systems, and media herein are not limited to comprising metal. Such objects, instruments, and/or surgical tools may contain any material that may be opaque or dense in a sense that they can obstruct anatomical information. In some embodiments, when the imaging modality is radiography or X-ray related, the objects, instruments and/or surgical tools can be radiodense. With other imaging modalities, the objects, instruments, and/or surgical tools may not contain any metal but may contain one or more types of other materials that obstruct the anatomical information.

In some embodiments, the metal objects herein are equivalent to opaque objects or dense objects with the specific imaging modality used. For example, the metal objects disclosed herein may comprise glass or plastic which is opaque when the imaging modality is Ultrasound.

In some embodiments, the portion of a 2D image blocked by the metal instruments can be replaced with the prediction at the blocked pixels. Assuming sufficiently-accurate alignment, the prediction of the image content can display the missing anatomy hidden by the metal object(s), thereby rendering that metal object(s) "translucent." The displayed result can be calculated as a linear combination of the original 2D image with metal and predicted information with a first set of blocked anatomy, thus providing a translucent or transparent effect to the metal object(s). In some embodiments, the proportion or weighting of the combination can controlled by the user, for example, using a translucency "slider."

To account for inaccuracy in the registration of the 3D scan to the 2D image, in some embodiments, anatomy that are not blocked by metal objects can be used to find an optimal registration. In some cases, the hypothesized view orientation through the 3D dataset to generated the predicted 2D image can be varied until the generated 2D image has a strong enough similarity (for example, by calculating the cross-correlation) to the actual 2D image for pixels that are not blocked by metal objects. This registration correction can account for translational and rotational errors, or even other errors caused by non-rigid transformation.

In some embodiments, the qualitative appearance of the prediction-generated anatomy may require adjustment to match sufficiently to the 2D image's anatomy. As non-limiting examples, the brightness, contrast, gray-level histogram, and other image characteristics can be adjusted so that the prediction-rendered anatomy is not distractingly different looking than the real 2D image. Alternatively, it may be desirable for the artificially-rendered anatomy to look different than the real anatomy to avoid errors in interpretation. In these particular embodiments, the prediction-rendered pixels can be intentionally adjusted (e.g. using differing brightness or false color) to distinguish them.

Figure 1D:
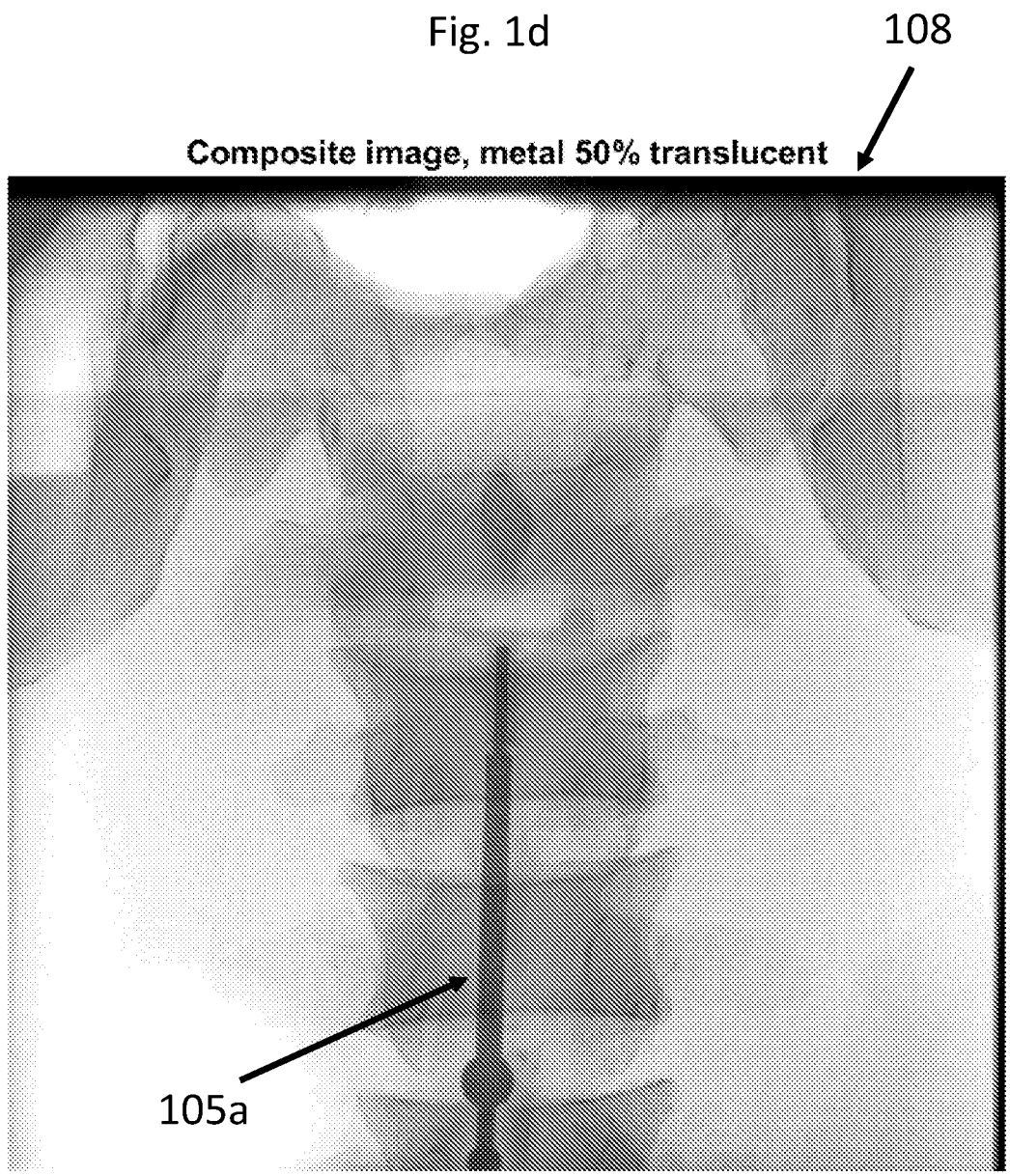
FIG. 1d shows an improved 2D X-ray image of FIG. 1a, in which the metal object(s) is 50% translucent, in accordance with embodiments herein.

FIGS. 1a-1e shows exemplary images of the systems, methods and media disclosed herein. In this particular embodiment, a 2D Radiographic image 105 acquired using a C-arm device includes object(s) 105a, e.g., surgical instruments that contains metal, as shown in FIG. 1a. In order to erase the object(s) 105a and recover anatomical information blocked by them, a 3D image dataset 106, as shown in FIG. 1b can be registered to the 2D image space, and the information in the registered 3D dataset can be used to predict the anatomical information blocked by the objects 105a, thereby generating an improved 2D image with the objects completely removed, as in FIG. 1c, or with customized translucency determined by the user, as shown in FIG. 1d. A mask of the objects 105b as in FIG. 1e can be generated after identification of the pixels of the objects and may be used to determine the pixels that needs prediction information obtained from the 3D registered image dataset 106. Based on the output of a metal-classification algorithm, individual pixels in the 2D image can be automatically labeled as either likely to be occluded by metal or unlikely to be occluded by metal. Such labeling can also be done manually, in other words by a human after visual inspection of the image. Alternatively, the labeling can be automatic or semiautomatic. Only pixels that are labeled as metal are then replaced with the corresponding pixel from the 2D prediction image generated from the 3D volume image. This labeling can be Boolean, in other words distinctly either "metal" or "not metal", or can be continuously graded between "not metal" and "metal" according to the strength of belief that the pixel is occluded. In this case, the pixel can be replaced by a weighted sum of its original value and the value of the corresponding pixel in the 2D prediction image, with the weight chosen to be proportional to the labeling value. The value of the labels for each pixel in the 2D image can itself be assembled into another image (often denoted as a "mask" image). This mask image can be used as an indicator for later steps in the algorithm as to which pixels need to be replaced, and how. It can also be viewed to provide information about the accuracy of the metal-detection algorithm for a given image.

Figure 1E:
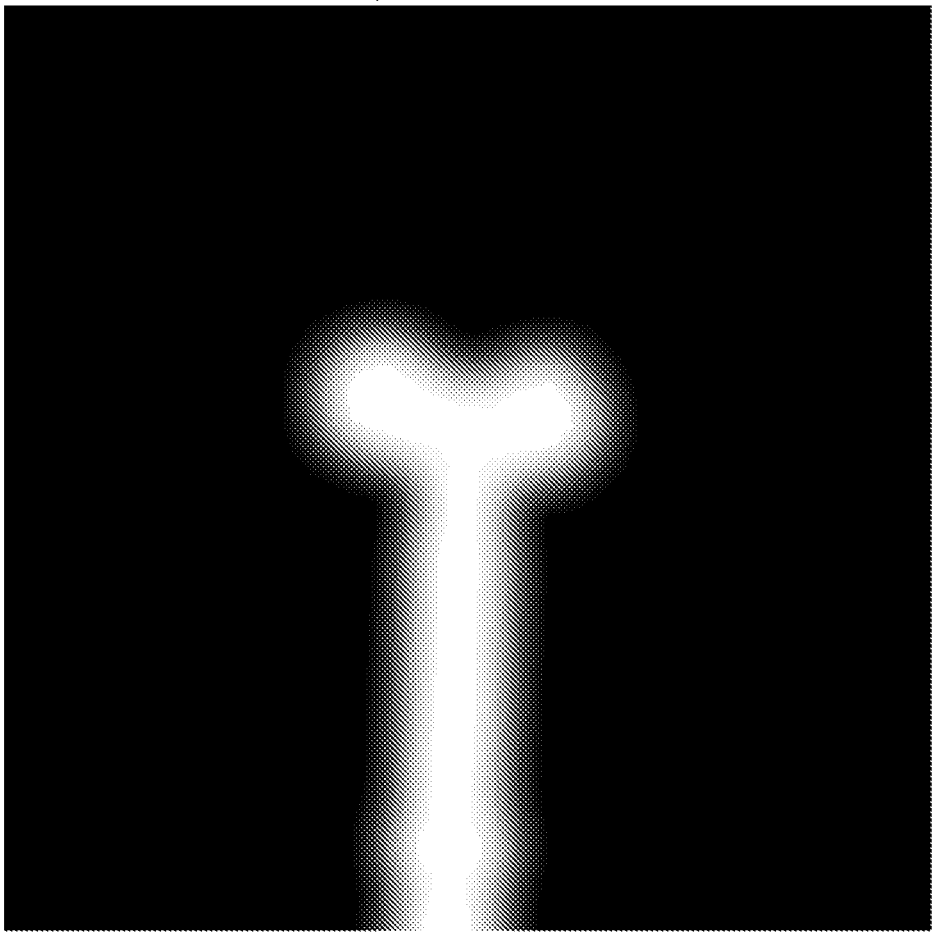
FIG. 1e shows an exemplary composite mask that can be used to generate the improved 2D X-ray images in FIGS. 1c-1d, in accordance with embodiments herein.
Figure 2:
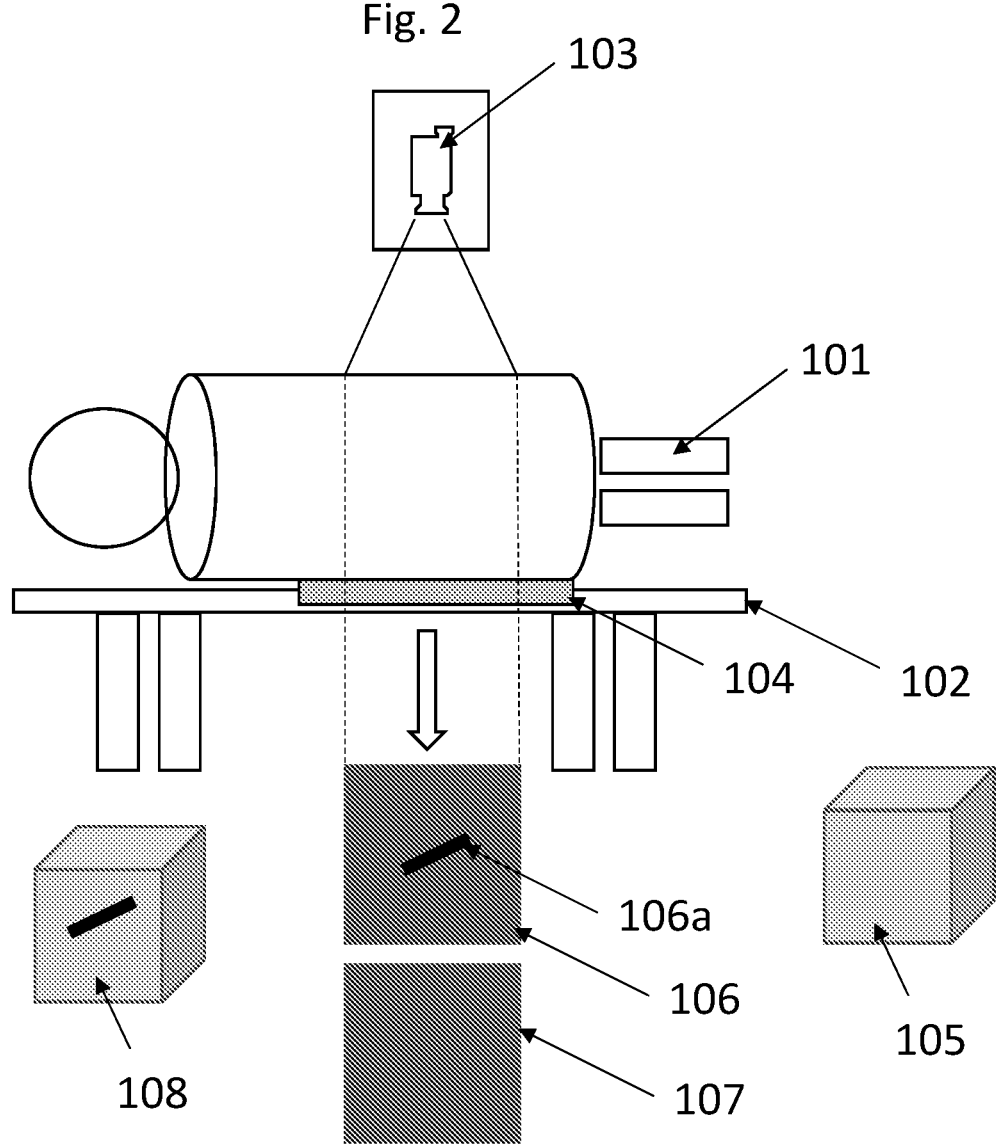
FIG. 2 shows a schematic diagram of the systems as disclosed herein, in accordance with embodiments herein.

Referring to FIG. 2, in a particular embodiment, the patient or otherwise the subject to be operated on 101 is positioned on a surgical bed 102 in a desired position, for example, lying on his or her side laterally. The image capturing device 103 is positioned manually or automatically so that it can include a designated region of the patient in its field of view. The image capturing device 103 can be a radiographic imaging device, such as a C-Arm or O-Arm. The image capturing device 103 can also include more than one imaging devices, for example, an X-ray imaging device and an infrared imaging device, or as another example, a MRI-PET scanner. The image sensor, image intensifier, or otherwise any device 104 that collects, intensifies, and/or reconstructs the image can be positioned on the surgical bed 102 or in other locations of the operation room. The image capturing device can generate 2D image(s) 105 of the subject, and such 2D images may have undesired objects 105a in the field of view blocking or obscuring part of the anatomical information of the subject. The objects 105a may be metal objects such as surgical instruments or any other objects that the surgeon or user wants to remove from the 2D image 105. The 3D image dataset 106 of the same subject may have already been acquired either during a prior visit, during the same visit but before the objects has been placed into the patient, or even during positioning of the patient. The 3D image dataset 106 may be registered to a 2D image space of the image capturing device 103, thus generating a registered 3D image dataset 107. Information from the registered 3D image dataset can be used to predict the anatomical information in the image pixels that are blocked by the objects 105a, In order to make the prediction, identification of the pixels of blocked anatomical information can be performed. As a non-limiting example, a binary mask as shown in FIG. 1e can be generated to determine the blocked pixels that needs prediction. The content or numerical value in such blocked pixels can be replaced using the prediction, and an improved 2D Radiographic image 108 can be generated using the predicted pixels.

Three-Dimensional (3D) Datasets

Disclosed herein, in some embodiments, the systems, methods, and/or media requires 3D dataset(s) of a subject for rendering metal objects translucent or otherwise manipulating the rendering of 2D images containing metal objects so that the anatomical information blocked by the metal objects can be accurately recovered in real-time. In some embodiments, such 3D dataset(s) are readily available to the user and do not need to be acquired for the sole purpose of rendering metal objects translucent. Thus, using the 3D datasets can be advantageous as no additional ionizing radiation needs to be introduced to the subject just for the sole purpose of rendering metal objects translucent. As a nonlimiting example, after a patient is positioned on a surgical bed, to confirm the anatomical region that needs to be operated on, a 3D dataset may be acquired and such 3D dataset can be used again in the systems, methods, and/or media disclosed herein. In some embodiments, when the full 3D dataset is not readily available to the user, at least part of the 3D dataset can be generated based on image data that has been acquired so that unnecessary radiation exposure to the subject can be avoided and the total amount of radiation is less than acquiring the entire 3D dataset only for rendering the metal objects translucent. Another advantage associated with using an existing 3D dataset is time and cost saving for both the user and the subject to be operated on as acquiring a 3D dataset may not occur in real-time, and the cost for image acquisition is not negligible. In some embodiments, when such 3D dataset is not readily available, a 3D dataset can be acquired with a method that introduces less or no radiation to the subject. For example, the 3D dataset may be acquired using non-radiative imaging modalities such as Magnetic Resonance Imaging and ultrasound.

As disclosed herein, the 3D dataset can be of various image parameters such as field of view, resolution, signal-to-noise ratio (SNR), contrast, brightness, and image size. In some embodiments, the 3D dataset can have a resolution that is comparable or higher than that of the 2D image that contains the metal objects. In some embodiments, the 3D dataset can have one or more image parameters that are approximately identical to that of the 2D image that contains the metal objects. For instances, the 3D dataset can have an identical resolution as the 2D image, or the 3D dataset may include a 3D field of view that at least partly includes the anatomical information blocked by metal object(s) in the 2D image. For other instances, the 3D dataset may include a 3D field of view that at least partly overlaps with the 3D volume that gets projected into the 2D image that contains the metal objects. For yet other instances, the 3D dataset may include a field of view that at least partly includes the set of anatomical information in 3D which, when projected into the 2D image, is blocked by the metal objects. The 3D dataset may include a field of view that at least partly includes the set of anatomical information in 3D which, when projected into the 2D image, is not blocked by the metal objects. As a non-limiting example, the 3D dataset has a field of view of 40 cm by 40 cm by 40 cm in order to cover the anatomy of the lower back of the subject. In this particular example, the resolution or voxel size is 0.2 cm by 0.2 cm by 0.2 cm, and the 3D dataset completely includes the 3D volume of anatomical structure that is projected into the 2D image.

In some embodiments, the 3D dataset may be acquired by one or more imaging modalities. Nonlimiting examples of the imaging modalities includes X-ray, Computerized Tomography (CT), CAT, MRI, ultrasound, Positron emission tomography (PET), Single-photon emission computed tomography (SPECT), Optical coherence tomography (OCT), fluorescence imaging, fluoroscopic imaging, and infrared imaging. The 3D dataset may or may not be acquired using the same imaging modality or modalities as the 2D image of the subject that contains metal objects.

In some embodiments, the 3D dataset may be acquired at any time prior to or during the medical procedure. For example, the 3D dataset may be acquired after proper positioning of the subject on the surgical bed but before any metal objects has been placed near or in the subject, so that the 3D dataset is free of the metal objects. In some embodiments, the 3D data set may be acquired with different metal objects as those in the 2D image or with the same metal objects as the 2D image but the metal objects are at different positions. In some embodiments, the 3D data set is acquired so that the anatomical information blocked by the metal object in the 2D image is at least partly available or unblocked in the 3D dataset.

In some embodiments, the 3D dataset may or may not be acquired using a projection based imaging modality so that the spatial resolution of the anatomy in the third dimension (e.g., thickness or height of an image voxel) is equal to or greater than a desired resolution. In some embodiments, the 3D dataset utilizes averaging (over multiple time points) or other signal processing methods to generate the 3D dataset that can be used by the systems, methods, and media herein. Nonlimiting examples of the other signal processing methods includes filtering, sampling, translation, rotation, segmentation, registration, and pattern recognition.

In some embodiments, the 3D dataset includes a plurality of 2D images of the subject, the 2D images are stacked in a third direction that is not parallel to the 2D images. In some embodiments, the 3D dataset includes a 3D volume image of the subject, in particular, the anatomical region to be operated on.

Two-Dimensional (2D) Images

Disclosed herein, the systems, methods, and media herein include at least one 2D image of the subject. The 2D image can be an image acquired using the image capturing device herein. The 2D image can contain one or more metal objects in its field of view. In some embodiments, the systems, methods, and media herein only require one 2D image with one or more metal objects in order to fill in the missing anatomical information blocked by the metal objects.

In some embodiments, the systems, methods, and media herein does not require any 2D image to be taken so that no additional radiation dosage needs to be introduced to the subject. The metal objects can be non-overlapping in one dimension or two dimensions in the 2D image. In other embodiments, the metal objects may be at least partly overlapping in the 2D image. In other embodiments, the metal objects are not overlapping in the 2D image.

The 2D image herein can be a projection image that contains a projection of anatomical structure from a 3D volume image of the subject. In other words, the 2D image can be formed by summing the intensity along all points in the 3D volume image along the perspective path for each 2D image pixel. The summation includes contributions from both anatomy and metal items, so the anatomical information behind or in front of the metal item along the perspective path is obscured.

In some embodiments, the 2D image may not need to be acquired, but only imaging information of the 2D image is obtained for the systems, methods, and media herein. Such imaging information of the 2D image can be used to obtain data from the 3D dataset, so that a prediction or estimation of the 2D image can be generated using the 3D data. As a nonlimiting example, instead of acquiring an actual 2D image of the subject, parameter(s) of the image capturing device, such as position, angle(s), penetration depth, can be used to generate a prediction or estimation of the entire 2D image. For example, if the image capturing device is positioned above a lateral side of the subject, as shown in FIG. 2, with the known field of view of the image capturing device and its penetration depth, a registered 3D image dataset of the subject can be used to predict or estimate how the entire 2D image would look like even if no 2D image has been taken yet.

As disclosed herein, the 2D image can be of various image parameters such as field of view, resolution, signal-to-noise ratio (SNR), contrast, and image size. As a nonlimiting example, the 2D image has a field of view of 40 cm by 40 cm. In this particular example, the resolution or pixel size is 0.5 cm by 0.5 cm. As another example, the image resolution or pixel size is at or less than 1 mm, e.g., 0.5 mm by 0.5 mm In some embodiments, the 2D dataset may be acquired by one or more imaging modalities. Nonlimiting examples of the imaging modalities including X-ray, Computerized Tomography (CT), CAT, MRI, ultrasound, Positron emission tomography (PET), Single-photon emission computed tomography (SPECT), Optical coherence tomography (OCT), fluorescence imaging, fluoroscopic imaging, and infrared imaging. The 3D dataset may or may not be acquired using the same imaging modality or modalities as the 2D image of the subject that contains metal objects.

Identification of Opaque Objects

In some embodiments, the systems, methods, and media herein includes identification of one or more objects in a 2D image. The one or more objects may be metal and/or surgical instruments. The identification may include identification of pixels that are completely or partially occupied by the object(s). The identification may include identification of contour(s) of the object(s). The identification may include learning from a sample dataset. The identification may include clustering the pixel into blocked pixels or unblocked pixels. The identification may utilize a software module, an application, an algorithm, a mathematical model, a statistical model, or the like. In some embodiments, such identification may be automatic, semi-automatic, or manual. In some embodiments, such identification utilizes artificial intelligence or machine learning. Such identification may utilize a supervised learning algorithm, an un-supervised learning algorithm, a reinforcement learning algorithm, a deep learning algorithm, or a neural network related algorithm. Such identification may require a training dataset.

Image Space

In some embodiments, the systems, methods, and media herein includes an image space or equivalent, an imaging space determined by the image capturing device, more particularly, the imaging parameter(s) or information of the image capturing device. In other words, the image space is portion of 3D space that projects to a point or pixel inside the 2D image boundary. The image space may change with change of the imaging parameter(s), e.g., capturing angle, capturing field of view, and/or movement of the subject relative to the image capturing device.

In some embodiments, the image space can be equivalent to a 2D or 3D field of view determined by the image capturing device. In that sense, the image space can be 2D with the information in the third dimension projected to a pixel inside the 2D field of view.

Anatomical Information

In some embodiments, the systems, methods, and media herein includes a first set of anatomical information that is blocked by object(s) in the 2D image. The first set of anatomical information can be from 3D anatomical structure when the 2D image is a projection image, such as a radiographic image. The first set of anatomical information can be from whatever structure(s) that is blocked by the metal objects and not visible in the 2D image disclosed herein. The first set of anatomical information may be useful to the user or otherwise the medical professional that is performing the procedure. Blockage of the first set of anatomical information may cause inconvenience, inaccuracy or even adverse events in the medical procedure.

In some embodiments, the systems, methods, and media herein includes a second set of anatomical information that is not blocked by metal object(s) in the 2D image. The second set of anatomical information is present in the 2D image and can be used to recover the first set of blocked information. In some embodiments, the second set of unblocked anatomical information can be used for evaluating the accuracy of registration of the 3D dataset to the image space. The second set of unblocked anatomical information can be used for evaluating the accuracy of prediction or estimation of the first set of blocked anatomical information. For example, after registration of the 3D dataset to the image space, estimation or prediction of the second set of unblocked anatomical information can be generated using the registered 3D dataset and compared to the actual second set of anatomical information in the 2D image to see how accurate the prediction or estimation is.

Registration

In some embodiments, the systems, methods, and media disclosed herein includes registering a 3D dataset or 3D volume to a 2D image or a 2D image space. In some embodiments, the systems, methods, and media disclosed herein includes registering a 3D data set or 3D volume to a coordinate system determined by the 2D image. In some embodiments, the systems, methods, and media disclosed herein includes registering the coordinate system of the 3D dataset to the coordinate system of the image space so that it can be determined how a 2D image may look like from the perspective of the image capturing device given the registered 3D dataset. In some embodiments, registration herein includes alignment of the 3D dataset with the 2D image space or alignment of the 2D image space with a 2D prediction image generated from the 3D dataset at a particular perspective.

Registration herein can include translation and/or rotation of one or more data points of the 3D dataset. Registration herein can utilize one or more reference points (e.g., infrared tracked metal pins) or other reference information (e.g., edge(s) of an anatomical feature, major axis such as axis of symmetry of anatomy, or anatomical structure, e.g., a vertebra, etc.). Such reference points can be external, such as metal pins or markers added to the subject or intrinsic to the subject.

In some embodiments, registration herein includes one or more of: translation, rotation, scaling, interpolation, non-rigid transformation, rigid transformation, linear transformation, non-linear transformation, mirror reflection, shear, and aspect ratio change.

In some embodiment, registration herein includes registering only part of the 3D dataset of the subject to the image space. For example, registration herein includes registering the vertebral bodies and anatomical structures close to the vertebral bodies, while other anatomical information, such as subcutaneous fat that can be easily deformed and/or have no or little relevance to the medical procedure are not registered. As another example, registration herein includes registering only a portion of the full width, length, or thickness of the 3D dataset, e.g., excluding the last 4 voxels on the edges of the 3D dataset. In some embodiments, registration herein includes registering the complete 3D dataset of the subject to the image space.

Image Capturing Devices

The systems, methods, and media disclosed herein includes an image capturing device. The image capturing device can be any device that is capable of capturing data that can be used to generate a medical image of the subject. The image capture device can utilize one or more imaging modalities. For example, the image capturing device can include a Radiographic imaging device and an ultrasound imaging device. As another example, the image capture device can be an imaging scanner, such as an X-ray image intensifier or a C-arm. In some embodiments, the image capturing device can include a camera. The camera may utilize visible light, infrared light, other electro-magnetic waves in the spectrum, X-ray, or other sources.

In some embodiments, the image capturing device is in communication with the systems, methods, and media herein for data communication, or operational control of the image capturing device.

In some embodiments, the image capturing device includes an imaging sensor for detecting signal, e.g., visible light, x-ray, radio frequency (RF) pulses for generating the image(s). In some embodiments, the image capturing device includes one or more software modules for generating images using signal detected at the imaging sensor. In some embodiments, the image capturing device include a communication module so that it communicates data to the system, the digital processing device, a digital display, or any other devices disclosed herein.

Metal Objects

In some embodiments, the objects disclosed herein are metal objects. In some embodiments, the objects disclosed herein contain metal. In some embodiments, the objects herein are objects necessary for the medical procedure. In some embodiments, the objects herein include surgical instruments. As a nonlimiting example, the objects herein are objects for facilitating positioning of the patient, locating the anatomical region to be operated on, and providing fiducial markers for imaging and/or operation. Such objects can include but are not limited to retractors, retractor blades, set screws, bone screws, pile drivers, inserters, and spinal rods.

In some embodiments, the objects disclosed herein are not metal objects or do not contain any metal. The objects herein can be any objects that the medical professional or otherwise the user of the system intended to remove or render translucent.

In some embodiments, the objects are external objects to the subject. In some embodiments, the objects may be internal tissue/organ of the subjects. For example, the objects can include an implant that was implanted during a previous medical procedure.

Presentation of Images

The presentation of images disclosed herein can be customized to optimize the presentation of information to the surgeon or otherwise user of the systems in order to facilitate the medical procedure. As an example, the presentation may include presenting the original 2D image with objects and the improved 2D image without objects but recovered anatomical information side by side to the surgeon. As another example, presentation may include presenting the 2D improved image and with visual indication (e.g., an added contour, a pseudo color, etc.) of information that are generated based on prediction. In some cases, the prediction of the set of blocked anatomical information is presented as an overlay superimposed on the original two-dimensional image. As another example, presentation may include presenting the 2D improved image with a customized translucency of the set of blocked anatomical information.

Steps of Rendering the Opaque Objects Translucent

In some embodiments, the methods of rendering the metal objects translucent or otherwise recovering the anatomical information blocked by the metal objects includes one or more steps. The steps herein may or may not be in the order presented herein.

In some embodiments, the methods herein include one or more steps selected from: receiving, by a computer, a 3D dataset of a subject, if a 3D dataset is not readily available, the methods herein further include acquiring a 3D dataset using the image capturing device(s) disclosed herein; determining, by the computer, a 2D image space of an image capturing device, where the image capturing device is configured to generate a two-dimensional image of the subject from the image space. The methods herein optionally include acquiring a two-dimensional image of the subject from the image space and optionally receiving, by the computer, the two-dimensional image of the subject from the image capture device; registering, by the computer, the three-dimensional dataset of the subject to the image space of the image capturing device, thereby generating a registered three-dimensional dataset; predicting, by the computer, at least part of the two-dimensional image of the subject using the registered three-dimensional dataset (and the imaging parameters of the imaging capturing device if the 2D image is not acquired), wherein the at least part of the two-dimensional image of the subject includes one or more metal objects, and wherein the prediction of the at least part of the two-dimensional image of the subject includes a first set of anatomical information of the subject that is blocked by the one or more metal objects. The methods herein may further include generating, by the computer, an improved two-dimensional image of the subject based on the two-dimensional image and the prediction of the at least part of the two-dimensional image of the subject. In some embodiments, generating the improved two-dimensional image of the subject comprises: identifying, by the computer, a plurality of pixels that at least partly contains the one or more metal objects; optionally modifying, by the computer, data of the plurality of pixels; and combining, by the computer, the prediction of the at least part of the two-dimensional image of the subject and the data of the plurality of pixels, pixel by pixel.

In some embodiments, the methods further comprise adjusting registration of the three-dimensional dataset of the subject to the image space of the image capturing device until prediction of a second set of unblocked anatomical information of the two-dimensional image satisfies a predetermined criterion; and adjusting registration of the three-dimensional dataset of the subject to the image space of the image capturing device comprises calculating a similarity of the prediction of the second set of unblocked anatomical information to the second set of unblocked anatomical information in the two-dimensional image.

One or more steps of the methods disclosed herein can be performed in real-time. One or more steps can be performed so that no perceivable delay can be detected by the technician, surgeon, or otherwise user of the systems. One or more steps can be performed so that no perceivable delay exist in performing the medical procedure.

In some embodiments, real-time performance disclosed herein include a very small delay of less than 1 second, 0.8 seconds, 0.6 seconds, 0.5 seconds, 0.4 seconds, 0.3 seconds, 0.2 seconds, 0.1 seconds, 0.08 seconds, 0.06 seconds, 0.05 seconds, 0.02 seconds, or 0.01 seconds. In some embodiments, real-time performance disclosed herein includes a very small delay of less than about 1 second, 0.8 seconds, 0.6 seconds, 0.5 seconds, 0.4 seconds, 0.3 seconds, 0.2 seconds, 0.1 seconds, 0.08 seconds, 0.06 seconds, 0.05 seconds, 0.02 seconds, or 0.01 seconds. The time delay herein can be the time duration from the onset of a step to the end of the same step, or any subsequent step(s).

As a non-limiting example, a 2D X-ray image with metal objects is presented to a surgeon on a digital display in the operating room, the surgeon starts the software module on a digital processing device for recovering the blocked anatomical information. The software generates a registered 3D dataset using a readily available 3D X-ray image dataset of the patient, predicts the blocked pixels using the registered 3D dataset, and generates an improved 2D X-ray image. The improved 2D X-ray image is then present to the surgeon together with the original 2D image to the surgeon. The software completes all these steps in less than about 0.1 seconds.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 3:
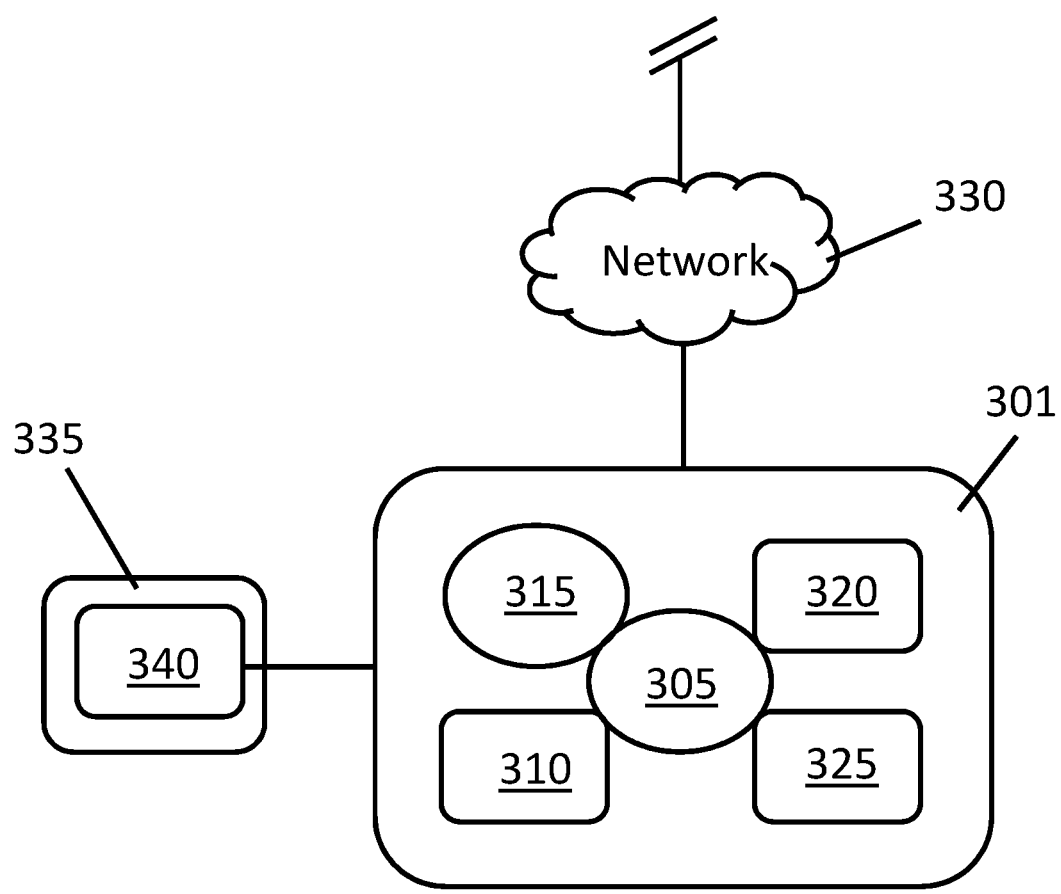
FIG. 3 shows a non-limiting example of the digital processing device as disclosed herein, in accordance with embodiments herein.

Referring to FIG. 3, in a particular embodiment, an exemplary digital processing device 301 is programmed or otherwise configured to estimate visual acuity of a subject. The device 301 can regulate various aspects of the algorithms and the method steps of the present disclosure. In this embodiment, the digital processing device 301 includes a central processing unit (CPU, also "processor" and "computer processor" herein) 305, which can be a single core or multi core processor, or a plurality of processors for parallel processing. The digital processing device 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The digital processing device 301 can be operatively coupled to a computer network ("network") 330 with the aid of the communication interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330, in some cases with the aid of the device 301, can implement a peer-to-peer network, which may enable devices coupled to the device 301 to behave as a client or a server.

Continuing to refer to FIG. 3, the CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and write back. The CPU 305 can be part of a circuit, such as an integrated circuit. One or more other components of the device 301 can be included in the circuit. In some embodiments, the circuit is an application specific integrated circuit (ASIC) or a field programmable gate array (FPGA).

Continuing to refer to FIG. 3, the storage unit 315 can store files, such as drivers, libraries and saved programs. The storage unit 315 can store user data, e.g., user preferences and user programs. The digital processing device 301 in some cases can include one or more additional data storage units that are external, such as located on a remote server that is in communication through an intranet or the Internet.

Continuing to refer to FIG. 3, the digital processing device 301 can communicate with one or more remote computer systems through the network 330. For instance, the device 301 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 301, such as, for example, on the memory 310 or electronic storage unit 315. The machine executable or machine readable code can be provided in the form of software. During use, the code can be executed by the processor 305. In some embodiments, the code can be retrieved from the storage unit 315 and stored on the memory 310 for ready access by the processor 305. In some situations, the electronic storage unit 315 can be precluded, and machine-executable instructions are stored on memory 310.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some embodiments, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable compiled applications.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application.

In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of acuity chart, acuity subchart, preliminary information of a subject, chart data of a subject, input and/or output of algorithms herein etc. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Although certain embodiments and examples are provided in the foregoing description, the inventive subject matter extends beyond the specifically disclosed embodiments to other alternative embodiments and/or uses, and to modifications and equivalents thereof. Thus, the scope of the claims appended hereto is not limited by any of the particular embodiments described herein. For example, in any method disclosed herein, the operations may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the systems, and/or devices described herein may be embodied as integrated components or as separate components.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "and," "or" herein is intended to encompass "and/or" unless otherwise stated. As used in this specification and the claims, unless otherwise stated, the term "about," and "approximately" can refers to variations of less than or equal to +/−1%, +/−2%, +/−3%, +1-4%, +1-5%, +1-6%, +1-7%, +1-8%, +1-9%, or +/−10% depending on the embodiment. As used in this specification and the claims, unless otherwise stated, the term "about," and "approximately" can refers to variations of less than or equal to +/−11%, +/−12%, +/−14%, +/−15%, or +/−20% depending on the embodiment. As a non-limiting example, about 100 meters can represent a range of 95 meters to 105 meters or 90 meters to 110 meters depending on the embodiments.

All publications, patents, and patent applications mentioned in this specification are herein incorporated by reference to the same extent as if each individual publication, patent, or patent application was specifically and individually indicated to be incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method for rendering metal objects translucent in medical images, the method comprising:
   receiving, by a computer, a three-dimensional dataset of a subject;
   determining, by the computer, an imaging space of an image capturing device, wherein the image capturing device is configured to generate a two-dimensional image of the subject from the imaging space;
   acquiring, by the image capturing device, a two-dimensional image of the subject from the imaging space;
   registering, by the computer, the three-dimensional dataset of the subject to the imaging space of the image capturing device, thereby generating a registered three-dimensional dataset; and
   predicting, by the computer, at least part of the two-dimensional image of the subject using the registered three-dimensional dataset, wherein the at least part of the two-dimensional image of the subject includes one or more metal objects, and wherein the prediction of the at least part of the two-dimensional image of the subject includes a first set of anatomical information of the subject that is blocked by the one or more metal objects.

2. The method of claim 1, further comprising receiving, by the computer, the two-dimensional image of the subject from the image capturing device.

3. The method of claim 2, further comprising, subsequent to the step of predicting at least a part of the two-dimensional image of the subject, generating, by the computer, an improved two-dimensional image of the subject based on the two-dimensional image and the prediction of the at least part of the two-dimensional image of the subject.

4. The method of claim 3, wherein the improved two-dimensional image is unobscured by the one or more metal objects, and wherein the improved two-dimensional image includes the first set of anatomical information of the subject.

5. The method of claim 3, wherein generating the improved two-dimensional image of the subject comprises:
   identifying, by the computer, a plurality of pixels that at least partly contains the one or more metal objects;
   optionally modifying, by the computer, data of the plurality of pixels; and
   combining, by the computer, the prediction of the at least part of the two-dimensional image of the subject and the data of the plurality of pixels pixel by pixel.

6. The method of claim 3 further comprising, presenting, by a digital display, the improved two-dimensional image to a user during a medical procedure.

7. The method of claim 6, wherein presenting the improved two-dimensional image comprises presenting the prediction of the first set of blocked anatomical information as an overlay superimposed on the two-dimensional image thereby facilitating the medical procedure.

8. The method of claim 2, wherein the two-dimensional image is an X-ray image, and wherein the one or more metal objects block the first set of anatomical information of the subject therewithin.

9. The method of claim 8 further comprising adjusting registration of the three-dimensional dataset of the subject to the imaging space of the image capturing device until prediction of a second set of unblocked anatomical information of the two-dimensional image satisfies a pre-determined criterion.

10. The method of claim 9, wherein adjusting registration of the three-dimensional dataset of the subject to the imaging space of the image capturing device comprises calculating a similarity of the prediction of the second set of unblocked anatomical information to the second set of unblocked anatomical information in the two-dimensional image.

11. The method of claim 2, wherein the two-dimensional image is generated using projection imaging, and wherein the one or more metal objects block the first set of anatomical information of the subject within the two-dimensional image.

12. The method of claim 1, wherein the three-dimensional dataset includes a CT dataset, a Magnetic Resonance Imaging dataset, a Positron Emission Tomography (PET) dataset, or an Ultrasound dataset of the subject.

13. The method of claim 12, wherein the three-dimensional dataset is acquired prior to a medical procedure of the subject that includes introduction of metal objects to the subject, or wherein the three-dimensional dataset is free of the one or more metal objects.

14. The method of claim 1, wherein one or more of: the registering of the three-dimensional dataset of the subject to the imaging space of the image capturing device; the prediction of the at least part of the two-dimensional image of the subject using the registered three-dimensional dataset; and the presentation of the improved two-dimensional image to the user is in real-time.

15. The method of claim 14, wherein the real-time includes a time duration of less than 1 second, 0.8 seconds, 0.6 seconds, 0.5 seconds, 0.4 seconds, 0.3 seconds, 0.2 seconds, 0.1 seconds, 0.08 seconds, 0.06 seconds, 0.05 seconds, 0.02 seconds, or 0.01 seconds.

16. The method of claim 1, wherein registering the three-dimensional dataset of the subject to the imaging space of the image capturing device comprises registering a first coordinate system of the three-dimensional dataset to a second coordinate system of the imaging space.

17. The method of claim 1, wherein the three-dimensional dataset is acquired with metal items within a field of view thereof, and wherein registering the three-dimensional dataset of the subject to the imaging space of the image capturing device comprises tracking the metal items using infrared light in the imaging space and registering the metal pins in the three-dimensional dataset to the metal pins in the imaging space.

18. A computer-implemented system comprising:
an image capturing device;
a digital processing device comprising a processor, a memory, and an operating system configured to perform executable instructions, the digital processing device in digital communication with the image capturing device; and
a computer program stored in the memory including instructions executable by the processor of the digital processing device to create a metal object removal application comprising:

a software module configured to receive a three-dimensional dataset of a subject;

a software module configured to determine by the computer, an imaging space of an image capturing device, wherein the image capturing device is configured to generate a two-dimensional image obtained of the subject from the imaging space;

a software module configured to register the three-dimensional dataset of the subject to the imaging space of the image capturing device, thereby generating a registered three-dimensional dataset; and a software module configured to predict at least part of the two-dimensional image of the subject using the registered three-dimensional dataset, wherein the at least part of the two-dimensional image of the subject includes one or more metal objects, and wherein the prediction of the at least part of the two-dimensional image of the subject includes a first set of anatomical information of the subject that is blocked by the one or more metal objects.

19. A method for rendering objects translucent in medical images, the method comprising:
receiving, by a computer, a three-dimensional dataset of a subject;

determining, by the computer, an imaging space of an image capturing device, wherein the image capturing device is configured to generate a two-dimensional image of the subject from the imaging space;

registering, by the computer, the three-dimensional dataset of the subject to the imaging space of the image capturing device, thereby generating a registered three-dimensional dataset;

predicting, by the computer, at least part of the two-dimensional image of the subject using the registered three-dimensional dataset, wherein the at least part of the two-dimensional image of the subject includes one or more objects, and wherein the prediction of the at least part of the two-dimensional image of the subject includes a first set of anatomical information of the subject that is blocked by the one or more objects;

further comprising acquiring, by the image capturing device, a two-dimensional image of the subject from the imaging space; and receiving, by the computer, the two-dimensional image of the subject from the image capturing device;

further comprising, subsequent to the step of predicting at least a part of the two-dimensional image of the subject, generating, by the computer, an improved two-dimensional image of the subject based on the two-dimensional image and the prediction of the at least part of the two-dimensional image of the subject;

wherein the improved two-dimensional image is unobscured by the one or more objects, and wherein the improved two-dimensional image includes the first set of anatomical information of the subject; and wherein the one or more objects comprise metal.

20. The method of claim 19 is without introduction of a radiation dosage to the subject.

* * * * *